United States Patent [19]

Adler

[11] 4,158,916
[45] Jun. 26, 1979

[54] SUCTION APPARATUS

[76] Inventor: Harold A. Adler, 1457 Eastwind Cir., Westlake Village, Calif. 91361

[21] Appl. No.: 817,388

[22] Filed: Jul. 20, 1977

[51] Int. Cl.² ............................................. A61C 17/04
[52] U.S. Cl. ........................................ 32/33; 128/276
[58] Field of Search ............................ 32/33; 128/276

[56] References Cited
U.S. PATENT DOCUMENTS

| 530,556 | 12/1894 | Sherwin | 32/33 |
|---|---|---|---|
| 1,698,331 | 1/1929 | Gunter | 32/33 |
| 3,000,805 | 9/1961 | Carritt et al. | 128/276 |
| 3,324,855 | 6/1967 | Heimlich | 128/276 |
| 3,758,950 | 9/1973 | Krouzian | 32/33 |
| 4,083,115 | 4/1978 | McKelvey | 32/33 |

*Primary Examiner*—Louis G. Mancene
*Assistant Examiner*—Michael Foycik

[57] ABSTRACT

In combination with a suction apparatus to eject saliva from the mouth of a human being during dental procedures, an attachment to be attached to the open end of a suction tube. The attachment comprises a suction apparatus cover in the form of a cloth, a fine mesh screening or a porous plastic material which is to evenly distribute the application of the vacuum across the exterior surface of the cover.

2 Claims, 9 Drawing Figures

SUCTION APPARATUS

BACKGROUND OF THE INVENTION

The field of this invention relates to a suction apparatus and more particularly to a suction apparatus to be used in the field of dentistry to continuously remove saliva from a patient's mouth during dental procedures.

One of the commonly used tools at the present time within dentistry is the placing of an instrument within the patient's mouth to remove saliva that has generated during dental procedures. This keeps the accumulated saliva from hindering the procedures.

The suction apparatus this is conventionally employed constitutes an elongated conduit which has a head attached to the open end of the conduit. The head includes a pair of enlarged slots or openings and it is this head that is to be placed within the person's mouth and the saliva is to be drawn through the enlarged openings and into the conduit and subsequently disposed of.

A disadvantage of this type of device is that the mouth tissue of the patient is partially drawn into the enlarged openings. Not only does this hamper the function of the device, the patient experiences a significant discomfort and possibly some pain when the soft tissue on the floor of the mouth of the patient is drawn into the openings.

There is a definite need for a saliva ejector which removes the saliva but did not effect the tissue of the person's mouth.

SUMMARY OF THE INVENTION

An attachment is provided for use with a suction apparatus to be employed as a saliva ejector to be used in the field of dentistry which takes the form of an elongated tube or conduit which is connected to a head at its open end. The saliva is to be conducted through enlarged openings formed in the head and into the conduit. To evenly distribute the suction and prevent aspiration of the soft tissue of the patient's mouth into the suction apparatus, a suction apparatus cover in the form of a cloth, a porous layer of plastic, or fine mesh screening completely encases the head. The suction apparatus cover could be attached separately about the head or could be formed integral with the head.

The primary objective of this invention is to design a saliva ejector to alleviate the discomfort often encountered with conventional saliva ejectors which aspirate mouth tissue.

DETAILED DESCRIPTION OF THE SHOWN EMBODIMENT

Figure 1:
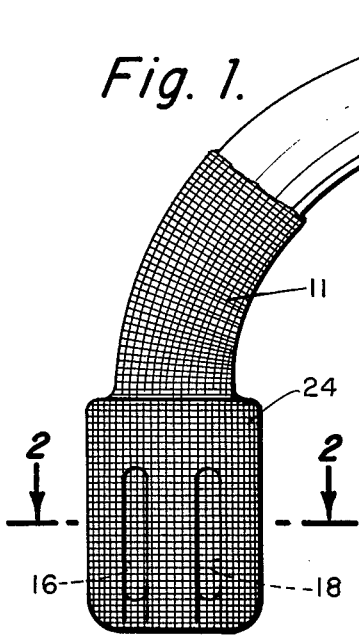
FIG. 1 is an elevation view of the first embodiment of saliva ejector apparatus of this invention.
Figure 2:
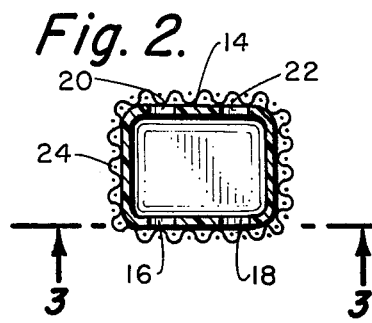
FIG. 2 is a cross-sectional view taken along line 2—2 of FIG. 1.
Figure 3:
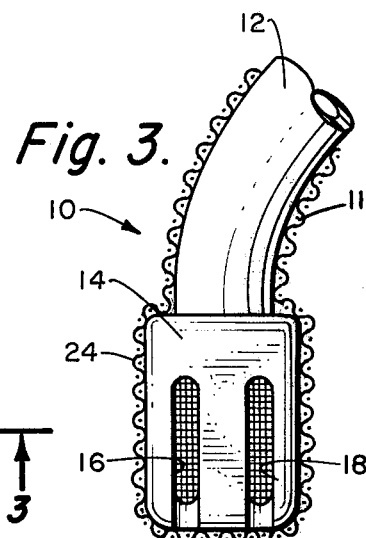
FIG. 3 is a view similar to FIG. 1 but with the front portion of the suction apparatus cover removed taken along line 3—3 of FIG. 2.

Referring particularly to the drawing, there is shown in FIG. 1 the saliva ejector apparatus 10 of this invention which takes the form of a conduit 12 and a head 14. The conduit 12 is to be connected to a vacuum apparatus and also to a saliva disposal source. A conventional technique for a source of vacuum and also for a saliva disposal source would be to a venturi within a water conduit with the movement of the water through the venturi creating the vacuum and also the water conduit functioning to remove and dispose of the saliva, water, blood, etc.

The conduit 12 as well as the head 14 will normally be constructed of a plastic material. However, it is to be understood thay any rigid material could be employed.

Figure 4:
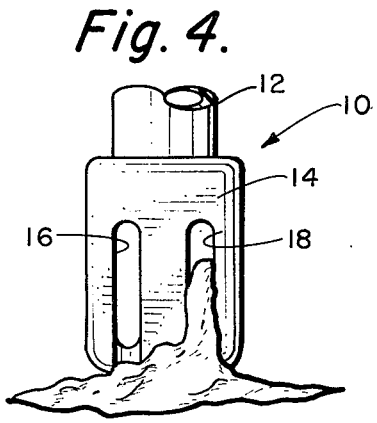
FIG. 4 is a diagrammatic view of a conventionally employed saliva ejector depicting aspiration of soft tissue into the device during use.
Figure 5:
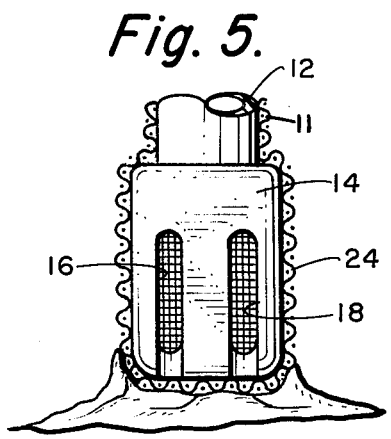
FIG. 5 is a view similar to FIG. 4 but showing the use of the device of this invention and non-aspiration of the tissue.

Within one face of the head 14 is located a pair of enlarged openings 16 and 18. A similar pair of openings 20 and 22 are located within the opposite face of the head 14. The head 14 will normally be placed within the patient's mouth and saliva is to be removed from the patient's mouth by being drawn through the openings 16, 18, 20 and 22 and through the conduit 12 to be disposed of. However, in normal practice, the soft tissue within a person's mouth may enter the openings as shown within FIG. 4. Not only does this clog the openings but the patient will experience some discomfort due to the aspiration of the tissue.

In order to prevent this aspiration, a nylon, rayon, wire or plastic screening mesh, slip-on cover 24 is used. The cover 24 is to be slipped over and completely encase the head 14 and will normally be secured to the tube 12, by means of a smaller diametered collar 11. The collar 11 will normally be elastic (also the main portion of the cover) to tightly grip the conduit 12. The screening material 24 not only assists in evenly distributing the vacuum across the exterior surface of the screening material, but also, because of the small openings within the screening material, there will be no tissue within the patient's mouth that will aspirate through openings 16, 18, 20 and 22. The cover 24 acts as a non-interfering surface between the head openings 16, 18, 20 and 22 and the tissue contacted, permitting free flow of air and liquid, but acting to exclude tissue and particulate matter from being drawn into the conduit 12.

Figure 6:
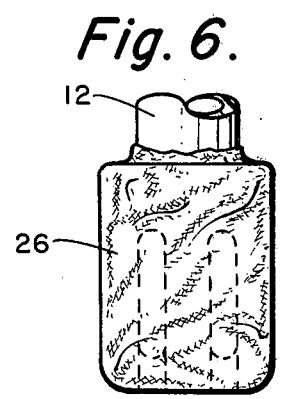
FIG. 6 is a view similar to FIG. 1 but showing the saliva ejector head covered by a cloth type of suction distribution material.

Referring particularly to FIG. 6, instead of the screening material 24, there may be employed a cloth material 26. This cloth material 26 could be a fabric cloth, but the preferrable type of cloth is a nylon or rayon such as is used in women's hosiery. The cloth material 26 is attached to the conduit 12 in much the same way as the screen material 24.

Figure 7:
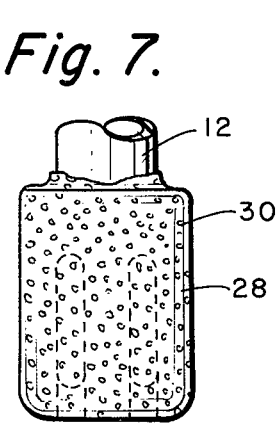
FIG. 7 is a view similar to FIG. 6 but showing a porous plastic cover for the head of the saliva ejector.

Referring particularly to FIG. 7, there is shown a layer of plastic 28 which can be employed in lieu of the screening 24 or the cloth 26. The plastic material 28 includes a substantial number of small sized openings 30 located entirely across the plastic material 28. Again, the attachment of the layer of plastic 28 about the head 14 is in the same manner as previously described.

Figure 8:
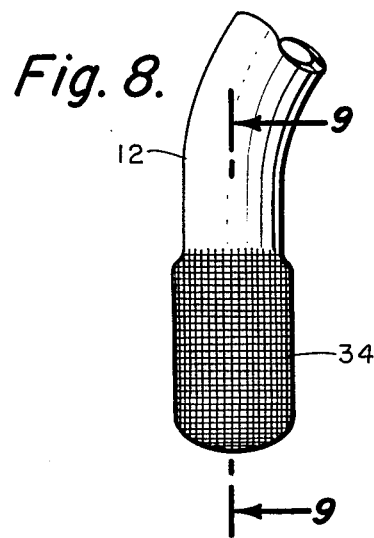
FIG. 8 is a view of a further modification of saliva ejector of this invention showing the apparatus cover being integrally attached to the end of the conduit.
Figure 9:
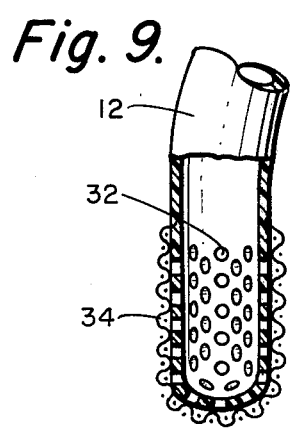
FIG. 9 is a cross-sectional view taken along line 9—9 of FIG. 8.

Referring particularly to FIGS. 8 and 9 of the drawing, the head of the device is altered in which the forwardmost section of the tube 12 is closed and includes a substantial number of holes 32. About the forwardmost end of the tube 12 and covering the hole 32 is a layer of screening 34. The screening 34 is to be integrally secured to the tube 12 and will be formed of a plastic material or the same material of construction of the tube 12.

What is claimed is:

1. A suction apparatus designed primarily as a saliva ejector for the mouth of a human being during dental procedures, said suction apparatus taking the form of an elongated tube through which a vacuum is applied, the elongated tube having an open end, a head attached to said tube at said open end, said head including enlarged openings to apply vacuum to the ambient, said head being larger in cross-section than said elongated tube, said head adapted to be located within the user's mouth, the improvement comprising:

a suction distribution means located about said head for substantially evenly distributing the application of vacuum across the exterior surface of said distribution means, said distribution means comprises an elastic cloth layer of material having a substantial number of small sized openings evenly distributed across said layer of material, said suction distribution means comprises an elastic cover which is readily slipped over and off of said head, said cover being tightly located about said head, said cover extending across said enlarged openings.

2. The apparatus as defined in claim 1 including:
said cover including an integral collar, said collar being in tight engagement with said elongated tube.